United States Patent [19]

Hanafusa et al.

[11] Patent Number: 5,679,617
[45] Date of Patent: Oct. 21, 1997

[54] AGENT AND METHOD FOR PRESERVING FRESHNESS OF CUT FLOWERS

[75] Inventors: Miho Hanafusa, Yokohama; Naoki Akiyama, Tokyo; Toshitake Kawakami, Tokyo, all of Japan

[73] Assignees: Mitsubishi Chemical Corporation; Astro Corporation, both of Tokyo, Japan

[21] Appl. No.: 590,904

[22] Filed: Jan. 24, 1996

[30] Foreign Application Priority Data

Jan. 31, 1995 [JP] Japan .................................. 7-014151

[51] Int. Cl.$^6$ ...................................................... A01N 3/02
[52] U.S. Cl. .............................................................. 504/115
[58] Field of Search ........................ 504/115; A01N 3/02

[56] References Cited

U.S. PATENT DOCUMENTS

| | | | |
|---|---|---|---|
| 3,947,383 | 3/1976 | Baggett | 260/2 BP |
| 4,802,905 | 2/1989 | Spector | 71/68 |
| 4,988,790 | 1/1991 | Behn et al. | 524/514 |
| 5,173,521 | 12/1992 | Ishino | 524/45 |
| 5,510,315 | 4/1996 | Kurotsu et al. | 504/115 |

*Primary Examiner*—S. Mark Clardy
*Attorney, Agent, or Firm*—Oblon, Spivak, McClelland, Maier & Neustadt, P.C.

[57] ABSTRACT

An agent for preserving freshness of cut flowers, which contains, as an active ingredient, at least one water-soluble polymer selected from the group consisting of:

i) a polycondensation product obtained by a reaction of (a) at least one compound selected from the group consisting of an epihalohydrin, an alkylene dihalide, a diepoxide and a dihalogenoalkyl ether, with (b) at least one compound selected from the group consisting of an amine, a diamine and a polyamine, ii) an alkyleneimine polymer, and iii) a mixture of the polymers i) and ii).

16 Claims, 2 Drawing Sheets

‡

‡

+

±

0

AGENT AND METHOD FOR PRESERVING FRESHNESS OF CUT FLOWERS

BACKGROUND OF THE INVENTION

1. Field of the Invention

The present invention relates to an agent and method for preserving freshness of live flowers, particularly cut flowers. More particularly, it relates to a (safe and inexpensive) agent and method for preserving cut flowers, whereby the period for enjoying cut flowers can substantially be prolonged by the effects of preventing deterioration in freshness due to e.g. wilting of petals or leaves of cut flowers, or yellowing of leaves and suppressing too much brooming, during the transportation of cut flowers after the harvest, at the distribution stage to e.g. retail, or at a consumer stage after the distribution. The freshness-preserving agent of the present invention is particularly effective for roses and chrysanthemums, for which no effective freshness-preserving agent has heretofore been available.

2. Discussion of Background

In recent years, consumption of cut flowers has increased for the purposes of e.g. business use, exercises of flower arrangements and domestic use to bring about enrichment of the human life. Accordingly, the necessity to prevent deterioration of freshness during the transportation or distribution from the production sites far from the consumers' areas or at the consumer stage, is very high. Further, it is very important to develop a freshness-preserving agent for one production site to excel other production sites.

Reagents to prolong the life of cut flowers may be generally classified into two types based on the stages of their use. Namely, one type is pretreating agents which are used for water uptake after the harvest by the producers, and the other type is post-treating agents which are used as added to water for cut flowers at the retail or consumer stage.

With respect to the post-treating agents, various products are commercially available which contain a fungicide, a surfactant and various nutrients such as inorganic salts, saccharide and nitrogen, as the main components.

As a pretreating agent, an aqueous solution of a silver thiosulfate complex (hereinafter referred to simply as STS) was reported by H. Veen, Netherlands, to have a high life-prolonging effect for cut flowers (H. Veen and S. C. Van de Geijn "Mobility and Ionic Form of Silver as Related to Congevity of Cut Carnations", Planta, 140, 93–96 (1978)). Since then, various STS agents have been commercially available also in Japan and widely used for cut flowers highly sensitive to ethylene known as a plant aging hormone, such as carnations, sweet peas, delfiniums and babies'-breaths. However, an environmental pollution by silver is feared.

On the other hand, the STS agents are not so effective for roses, chrysanthemums or transvaal daisies. Some freshness-preserving agents for such flowers are also commercially available, but their effects are not adequate.

Further, an agent containing a water-soluble quaternary ammonium-modified polysaccharide (or an aqueous solution containing a water-soluble quaternary ammonium-modified hydroxyalkyl polysaccharide) as an active ingredient (Japanese Unexamined Patent Publication No. 121201/1989) and an agent containing abscisic acid as an active ingredient (Japanese Unexamined Patent Publication No. 289501/1990) have been reported.

However, none of these agents is satisfactory in its freshness-preserving effect. Namely, the one containing a fungicide as the main component can hardly maintain its effect at the consumer stage after the distribution. The one containing silver as a component has a problem of a waste liquid which may be detrimental to the environment. The one containing a saccharide as the main component has a problem that clogging of xylem is likely to result due to bacteria in water in which cut flowers are dipped, thus leading to deterioration of freshness due to poor water take up. Thus, there have been problems yet to be solved.

SUMMARY OF THE INVENTION

It is an object of the present invention to solve such problems and to provide an (inexpensive) agent for preserving freshness of cut flowers, which has particularly high freshness-preserving effects for e.g. roses, chrysanthemums and transvaal daisies, for which the conventional silver thiosulfate complex (the STS agent) is not so effective, and which is substantially free from environmental pollution.

The present inventors have found that an agent for preserving freshness of cut flowers, which contains, as an active ingredient, a nitrogen-containing water-soluble polymer obtained by a reaction of at least one compound selected from the group consisting of an epihalohydrin, an alkylene dihalide, a diepoxide and a dihalogenoalkyl ether with at least one compound selected from the group consisting of an amine, a diamine and a polyamine, an alkyleneimine polymer, or a mixture of such polymers, exhibits a remarkable bent neck-preventing effect and an effect of prolonging the period for enjoying the flowers from budding to 80% blooming. The present invention has been accomplished on the basis of this discovery.

The object of the present invention can be accomplished by an agent for preserving freshness of cut flowers, which contains, as an active ingredient, at least one water-soluble polymer selected from the group consisting of:

i) a polycondensation product obtained by a reaction of (a) at least one compound selected from the group consisting of an epihalohydrin, an alkylene dihalide, a diepoxide and a dihalogenoalkyl ether, with (b) at least one compound selected from the group consisting of an amine, a diamine and a polyamine, ii) an alkyleneimine polymer, and iii) a mixture of the polymers i) and ii).

DETAILED DESCRIPTION OF THE PREFERRED EMBODIMENTS

Figure 1:
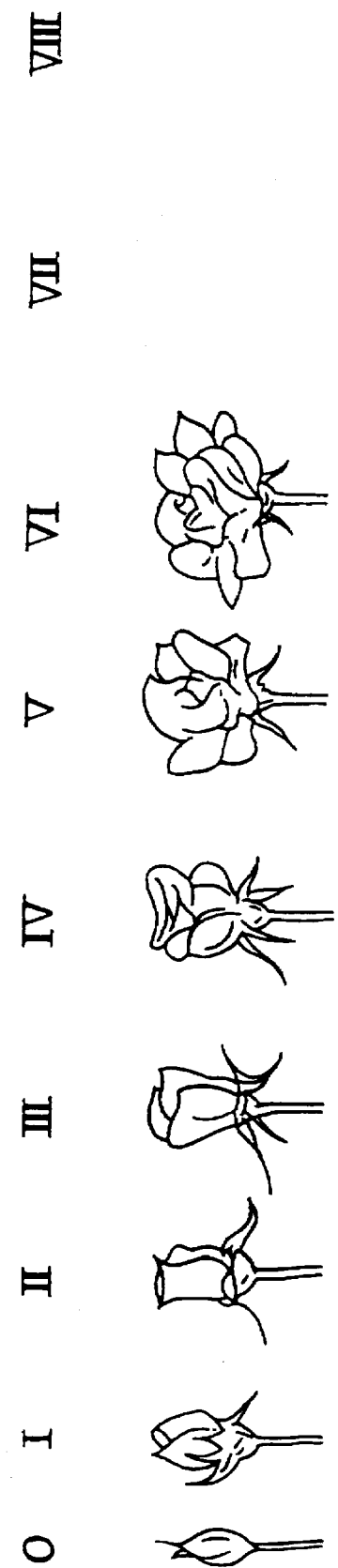
FIG. 1 shows the evaluation indexes and the blooming degrees of a rose used in Test Example 1.

Now, the present invention will be described in detail.

The amine, the diamine and the polyamine as starting materials for the nitrogen-containing water-soluble polymer to be used in the present invention, are preferably those of the following formula (1):

wherein each of $R^1$, $R^2$, $R^3$ and $R^4$ is a hydrogen atom or a $C_{1-3}$ linear or branched alkyl group, A is a $C_{1-6}$ linear or branched alkylene group, and n is an integer of from 0 to 5. Specific examples of the amine (n=0) include ammonia, methylamine, dimethylamine, dipropylamine, methylethylamine, methylpropylamine and ethylpropylamine. Specific examples of the diamine (n=1) include ethylenediamine, N,N-dimethylethylenediamine, N,N'-dimethylethylenediamine, N,N-diethylethylenediamine, propylenediamine, N,N-dimethylpropylenediamine, and N,N,N',N'-tetramethylethylenediamine. Likewise, specific examples of the polyamine (n=2–5) include diethylenetriamine, triethylenetriamine and tetraethylenepentamine. These amines, diamines and polyamines may be used in combination within or among the respective groups.

The epihalohydrin is the one represented by the formula (2):

wherein X is halogen. The halogen may, for example, be fluorine, chlorine, bromine or iodine in general. However, from the economical reason, epichlorohydrin is preferred.

The alkylene dihalide may be the one represented by the formula (3):

wherein B is a $C_{1-20}$ linear or branched alkylene group, and each of X and X' which may be the same or different, is halogen. Specifically, it includes, for example, dichloroethane, dichloropropane, dichlorobutane, dichlorohexane, dibromoethane, bromochloropropane, dibromopropane, dibromohexane and dichlorononane. Particularly preferred is 1,3-dichloropropane from the viewpoint of the reactivity with the amine and for the economical reason.

The diepoxide may, for example, be the one represented by the formula (4):

wherein D is a direct bond or a $C_{1-4}$ linear or branched alkylene group, or an ether group of the formula (5):

wherein m is an integer of from 1 to 4. Specifically, it includes, for example, 1,3-butadiene diepoxide, 1,4-pentadiene diepoxide, 1,5-hexadiene diepoxide, 1,6-heptadiene diepoxide, 1,7-octadiene diepoxide, ethylene glycol diglycidyl ether and triethylene glycidyl ether.

The dihalogenoalkyl ether may, for example, be the one represented by the formula (6):

wherein each of $R^5$ and $R^6$ is a $C_{1-4}$ linear or branched alkylene group, each of X and X' which may be the same or different, is halogen, and l is an integer of from 1 to 12. Specifically, it includes, for example, 2,2'-dichloroethyl ether, 2,2'-dibromoethyl ether, 3,3'-dichloropropyl ether, 2,3-dichloropropyl ether and 4,4'-dibromobutyl ether, when l=1, and it includes, for example, a dihalogenoethyl ether obtainable by a dehydration reaction from an ethylene oxide polymer having a degree of polymerization of up to 10 and a halogenated alkyl alcohol. Particularly preferred is 2,2'-dichloroethyl ether (hereinafter referred to as dichloroethyl ether) at least for the economical reason.

Such epihalohydrins, alkylene dihalides, diepoxides and dihalogenoalkyl ethers may be used alone or in combination as a mixture of two or more of them within the respective components.

To react the at least one compound selected from the group consisting of an epihalohydrin, an alkylene dihalide, a diepoxide and a dihalogenoalkyl ether, with an amine, it is preferred that the total molar amount of at least one compound selected from the group consisting of an epihalohydrin, an alkylene dihalide, a diepoxide and a dihalogenoalkyl ether, is adjusted to be substantially the same as the molar amount of the amine, and the reaction is carried out by using a closed type reactor equipped with a stirrer in the presence of a solvent in an inert gas atmosphere while maintaining the internal temperature of the reactor within a range of from 30° to 100° C.

More specifically, a 20 to 70% aqueous solution of an amine may be charged in a closed type reactor equipped with a stirrer, a reflux condenser, a thermometer, etc., the atmosphere in the reactor is replaced by nitrogen gas, and at least one compound selected from the group consisting of an epihalohydrin, an alkylene dihalide, a diepoxide and a dihalogenoalkyl ether, is continuously or stepwisely added with stirring while controlling the internal temperature of the reactor at a predetermined level.

As the solvent for the reaction, water is mainly used. However, in consideration of the solubility of the starting materials and the reaction products, methyl alcohol, ethyl alcohol or dimethylformamide may, for example, be used.

The water-soluble polymer may further be treated to convert the halogen as a counter ion (derived from the epihalohydrin, the alkylene dihalide and the dihalogenoalkyl ether) to another anion or to remove the counter ion, so that this polymer will then become a hydroxide.

The alkyleneimine polymer may be the one represented by the formula (7):

wherein $R^7$ is an alkylene group, preferably a $C_{1-8}$ linear or branched alkylene group, a plurality of $R^7$ may be the same or different, and n shows the degree of polymerization of this alkyleneimine polymer.

Such an alkyleneimine polymer may have a branch, as distinguished from the completely linear structure as represented by the above formula. Further, it may be a quaternary salt of an alkyleneimine polymer, having e.g. hydrochloric acid added to the alkyleneimine polymer.

Such an alkyleneimine polymer includes, for example, an ethyleneimine polymer, a propyleneimine polymer, a trimethyleneimine polymer, a tetramethyleneimine polymer, a hexamethyleneimine polymer and their copolymers as well as mixtures of two or more of them.

Among them, an ethyleneimine polymer is particularly preferred for the economical reason. The ethyleneimine polymer is usually obtained by ring-opening polymerization of ethyleneimine by a cationic catalyst. However, it may be obtained also by a reaction of an ethylene dihalide with ammonia, or a condensation reaction of ethanolamine.

The water-soluble polymer thus obtained is dissolved in a 2 mol/l KBr aqueous solution, and the intrinsic viscosity (η) is measured at 25° C. From the intrinsic viscosity, the molecular weight can be determined.

As the freshness-preserving agent of the present invention, the intrinsic viscosity (η) is usually from 0.02 dl/g to 2 dl/g, preferably 1.5 dl/g, more preferably from 0.02 dl/g to 1 dl/g. However, the intrinsic viscosity is not necessarily limited within such a range. (The intrinsic viscosity in the present invention is the one measured at 25° C. in a 2 mol/l KBr aqueous solution.)

The water-soluble polymer may be made into solid by removing the solvent (usually water). Otherwise, when it is produced in the form of an aqueous solution, the aqueous solution may be used as it is or after diluting or concentrating it, as the case requires.

The active ingredient of the present invention is not limited to the above-mentioned polymers and may be in the form of copolymers. Namely, it may be a copolymer obtained by a reaction of at least one compound selected from the group consisting of an epihalohydrin, an alkylene dihalide, a diepoxide and a dihalogenoalkyl ether, with an amine of the above-mentioned formula, an alkyleneimine polymer or a copolymer of the above polymer or copolymer with the above alkyleneimine polymer. In a case where the above polymer, the above copolymer and the above alkyleneimine polymer are used in combination as a mixture, the respective proportions are not particularly limited.

When the nitrogen-containing water-soluble polymer and the alkyleneimine polymer are used in combination as a mixture, the respective proportions are not particularly limited.

The freshness-preserving agent of the present invention may contain, in addition to the above described components, conventional additives such as a fungicide, a surfactant, and nutrients such as an inorganic salt, a saccharide, a nitrogen source, etc. Further, it may be used in combination with other conventional preserving agents.

The freshness-preserving agent of the present invention may be used as a pretreating agent or a post-treating agent for cut flowers.

When the freshness-preserving agent of the present invention is used as a pretreating agent, cut flowers after the harvest are dipped usually in an aqueous solution containing from 10 to 500,000 ppm, preferably from 50 to 50,000 ppm, more preferably from 100 to 5,000 ppm of the above water-soluble polymer. The temperature for the pretreatment is usually from 0° to 30° C., preferably from 2° to 20° C., more preferably from 5° to 15° C. The dipping time is preferably from 30 minutes to 100 hours, more preferably from one hour to 80 hours, most preferably from 2 hours to 75 hours, to obtain adequate effects.

When it is used as a post-treating agent, the above water-soluble polymer is added to water for cut flowers in an amount of from 5 to 5,000 ppm, preferably from 5 to 1,000 ppm, more preferably from 10 to 500 ppm.

The freshness-preserving agent of the present invention may be used either for the pretreatment or the post-treatment. When it is used as the pretreating agent, the effects are particularly excellent.

To the freshness-maintaining agent for cut flowers of the present invention, an inorganic metal salt such as aluminum sulfate or potassium aluminum sulfate, a saccharide such as glucose, fructose, sorbitol or polysaccharide, a nitrogen source, various fungicides, or plant hormones such as sitokanine, dibereline, abscisic acid or folic acid, may be incorporated, as the case requires.

Now, the present invention will be described in further detail with reference to Examples and Test Examples. However, it should be understood that the present invention is by no means restricted to such specific Examples.

Preparation Examples for Water-soluble Polymers (1) Sample A

Into a 50% dimethylamine aqueous solution, epichlorohydrin was added with stirring while maintaining the reaction temperature at 70° C. until the molar ratio of dimethylamine to epichlorohydrin became 1:1. The obtained mixed reaction composition (the composition having an intrinsic viscosity ($\eta$) of 0.20 dl/g) was diluted with water to obtain a sample having a purity of 50%, which was designated as sample A.

(2) Sample B

Into a 50% dimethylamine aqueous solution, epichlorohydrin was added with stirring while maintaining the reaction temperature at 80° C. until the molar ratio of dimethylamine to epichlorohydrin became 1:1. The obtained mixed reaction composition (the composition having an intrinsic viscosity ($\eta$) of 0.11 dl/g) was diluted with water to obtain a sample having a purity of 50%, which was designated as sample B.

(3) Sample C

Into a 50% dimethylamine aqueous solution, epichlorohydrin was added with stirring while maintaining the reaction temperature at 90° C., until the molar ratio of dimethylamine to epichlorohydrin became 1:1. The obtained mixed reaction composition (the composition having an intrinsic viscosity ($\eta$) of 0.06 dl/g) was diluted with water to obtain a sample having a purity of 50%, which was designated as sample C.

(4) Sample D

Into a 50% N,N,N',N'-tetramethylethylenediamine aqueous solution, epichlorohydrin was added with stirring while maintaining the reaction temperature at 80° C., until the molar ratio of N,N,N',N'-tetramethylethylenediamine to epichlorohydrin became 1:1. The obtained mixed reaction composition (the composition having an intrinsic viscosity ($\eta$) of 0.03 dl/g) was diluted with water to obtain a sample having a purity of 50%, which was designated as sample D.

(5) Sample E

Into a 50% N,N,N',N'-tetramethylethylenediamine aqueous solution, dichloroethyl ether was added with stirring while maintaining the reaction temperature at 70° C., until the molar ratio of N,N,N',N'-tetramethylethylenediamine to dichloroethyl ether became 1:1. The obtained mixed reaction composition (the composition having an intrinsic viscosity ($\eta$) of 0.08 dl/g) was diluted with water to obtain a sample having a purity of 50%, which was designated as sample E.

(6) Sample F

Into a 50% aqueous solution of a mixture of dimethylamine and diethylenetriamine in a molar ratio of 1:0.05, epichlorohydrin was added with stirring while maintaining the reaction temperature at 70° C., until the molar ratio of the 50% aqueous solution of the amine mixture to epichlorohydrin became 1:1. The obtained mixed reaction composition (the composition having an intrinsic viscosity ($\eta$) of 0.56 dl/g) was diluted with water to obtain a sample having a purity of 50%, which was designated as sample F.

(7) Sample G

Into a 50% dimethylamine aqueous solution, a mixture of ethylene glycol diglycidyl ether and dichloroethyl ether preliminarily prepared in a molar ratio of 1:1, was added with stirring while maintaining the reaction temperature at 70° C., until the molar ratio of the 50% dimethylamine aqueous solution to the mixture of ethylene glycol diglycidyl ether and dichloroethyl ether became 1:1. The obtained mixed reaction composition (the composition having an intrinsic viscosity ($\eta$) of 0.09 dl/g) and a mixed reaction composition (a composition having an intrinsic viscosity ($\eta$) of 0.07 dl/g) obtained by adding and mixing nitrogen and an equimolar amount of hydrochloric acid to an ethyleneimine polymer ("Epomin", tradename, manufactured by Nippon Shokubai Kagaku Kogyo K.K., grade SP-300) under cooling, were mixed in a ratio of 1:1, and the mixture was diluted with water to obtain a sample having a purity of 50%, which was designated as sample G.

By using the above samples, freshness-preserving agents of the present invention were prepared.

EXAMPLE 1: Sample A was diluted 1000 times to obtain a 500 ppm aqueous solution.

EXAMPLE 2: Sample B was diluted 1000 times to obtain a 500 ppm aqueous solution.

EXAMPLE 3: Sample C was diluted 1000 times to obtain a 500 ppm aqueous solution.

EXAMPLE 4: Sample D was diluted 1000 times to obtain a 500 ppm aqueous solution.

EXAMPLE 5: Sample E was diluted 1000 times to obtain a 500 ppm aqueous solution.

EXAMPLE 6: Sample F was diluted 1000 times to obtain a 500 ppm aqueous solution.

EXAMPLE 7: Sample G was diluted 1000 times to obtain a 500 ppm aqueous solution.

EXAMPLE 8: An aqueous solution containing 500 ppm of sample A and 100 ppm of aluminum sulfate, was prepared.

EXAMPLE 9: An aqueous solution containing 500 ppm of sample A and 500 ppm of glucose, was prepared.

COMPARATIVE EXAMPLE 1: City water

COMPARATIVE EXAMPLE 2: Commercial product A (main components: silver nitrate, RNA decomposition products and trishydroxymethylaminomethane)

COMPARATIVE EXAMPLE 3: Commercial product B (main components: aluminum sulfate and a fungicide)

COMPARATIVE EXAMPLE 4: Commercial product C (main components: sodium cis-propenyl phosphonate and a fungicide)

COMPARATIVE EXAMPLE 5: An aqueous solution containing 500 ppm of trimethylstearylammonium chloride (manufactured by Tokyo Kasei K.K.)

COMPARATIVE EXAMPLE 6: An aqueous solution containing 500 ppm of hydroxyethylcellulose hydroxypropyltrimethylammonium chloride, as one of quaternary ammonium-modified polysaccharides (manufactured by Lion Corporation)

COMPARATIVE EXAMPLE 7: An aqueous solution containing 500 ppm of polyvinyl alcohol having a polymerization degree of about 500 (manufactured by Wako Junyaku Kogyo K.K.).

COMPARATIVE EXAMPLE 8: An aqueous solution containing 500 ppm of polyethylene glycol 20000 (manufactured by Wako Junyaku Kogyo K.K.).

In each of Examples and Comparative Examples, city water was used for dilution.

TEST EXAMPLE 1

Freshness-preserving Effects for Roses

Roses (variety: roterose) were harvested and then dipped in the aqueous solutions of Examples 1 to 9 and Comparative Examples 1 to 8, respectively, at 8° C. for 5 hours in the dark. Then, they were packed in corrugated cardboard boxes and left overnight at 25° C. (which corresponds to transportation in a dry system). Then, they were put into plastic vases containing 2 l of city water, in groups each consisting of five flowers and subjected to storage tests at 25° C. under a relative humidity of 70% and an optical condition of 1200 1× (12 hr/12 hr). The tests were carried out in two series for each sample.

Figure 2:
FIG. 2 shows the evaluation indexes and the bent neck degrees of a rose used in Test Example 1.
Figure 2:
Figure 2:

The blooming degree and the bent neck degree were observed everyday. The results are shown in Table 1. In Table 1, the blooming degree was evaluated by using the blooming stages (I to VIII) shown in FIG. 1 as the indexes, and the bent neck was evaluated using the bent neck degrees (o to +++) shown in FIG. 2 as the indexes.

TABLE 1

| | Blooming degree and bent neck degree | | | | | | | | | | | | Period for enjoying flowers (days) |
|---|---|---|---|---|---|---|---|---|---|---|---|---|---|
| | After transportation | 1 day later | 2 days later | 3 days later | 4 days later | 5 days later | 6 days later | 7 days later | 8 days later | 9 days later | 10 days later | 11 days later | |
| Example 1 | I | II | III | IV | IV | V | V | V | VI | VI | VI | VIII | 10 |
| Example 2 | I | II | III | IV | IV | V | V | V | VI | VI | VI | VIII | 10 |
| Example 3 | I | II | III | IV | IV | V | V | VI | VI | VII | VII | VIII | 10 |
| Example 4 | I | II | III | IV | IV | V | VI | VI | VII | VIII | | | 8 |
| Example 5 | I | II | III | IV | IV | V | V | VI | VI | VIII | | | 8 |
| Example 6 | I | II | III | IV | IV | V | V | VI | VI | VII | VII | VIII | 10 |
| Example 7 | I | II | III | IV | IV | V | V | VI | VI | V | VIII | | 9 |
| Example 8 | I | II | III | IV | IV | V | V | V | VI | VI | VI | VIII | 10 |
| Example 9 | I | II | III | IV | IV | V | V | VI | VI | VII | VII | VIII | 10 |
| Comparative Example 1 | I | II | III | IV | IV | IV+ | VIII +++ | | | | | | 4 |
| Comparative Example 2 | I | III | IV | V | VI | VI | VII | VII+ | VIII ++ | | | | 6 |
| Comparative Example 3 | I+ | III | IV | IV | V | VII | VII+ | VIII ++ | | | | | 5 |
| Comparative Example 4 | I | II | III | IV | IV | IV+ | VIII ++ | | | | | | 4 |
| Comparative Example 5 | I± | II | III | IV | V | V | VI | VI | VIII ++ | | | | 6 |
| Comparative Example 6 | I+ | II | III | IV | IV | VIII ++ | | | | | | | 4 |
| Comparative Example 7 | I | II | III | IV | IV | IV+ | VIII ++ | | | | | | 4 |
| Comparative Example 8 | I | II | III | IV | V | V+ | VII+ | | | | | | 4 |

It is evident from Table 1 that the agents for preserving freshness of cut flowers of the present invention have excellent effects to delay the blooming of cut flowers of roses and to prevent the bent neck.

TEST EXAMPLE 2

Freshness-preserving Effects for Chrysanthemums

Chrysanthemums (variety: Seiun) were harvested and then dipped in the aqueous solutions of Examples 1 to 3 and Comparative Examples 1 and 5, respectively, at 8° C. for 5 hours in the dark. Then, they were packed in corrugated cardboard boxes overnight at 25° C. Then, they were put into plastic vases containing 2 l of city water, in groups each consisting of five flowers and subjected to storage tests at 25° C. under a relative humidity of 70% and an optical condition of 1200 1× (12 hr/12 hr). The tests were carried out in two series for each sample.

The wilting degrees of petals and leaves were observed everyday. The results are shown in Tables 2 and 3. In Tables 2 and 3, the wilting degrees were evaluated by the following five ratings.

4: No wilting
3: Slight wilting
2: Moderate wilting
1: Substantial wilting
0: Severe wilting

TABLE 2

|  | 5 days later | 6 days later | 7 days later | 8 days later | 9 days later | 10 days later | 11 days later | 12 days later |
|---|---|---|---|---|---|---|---|---|
| Example 1 | 4 | 4 | 4 | 4 | 4 | 3.5 | 3.5 | 3 |
| Example 2 | 4 | 4 | 4 | 4 | 3.5 | 3.5 | 3 | 3 |
| Example 3 | 4 | 4 | 4 | 4 | 3.5 | 3 | 3 | 2.5 |
| Comparative Example 1 | 4 | 3.5 | 3 | 2 | 2 | 1.5 | 1 | 1 |
| Comparative Example 5 | 4 | 4 | 3.5 | 3.5 | 3 | 2.5 | 2 | 2 |

TABLE 3

|  | 5 days later | 6 days later | 7 days later | 8 days later | 9 days later | 10 days later | 11 days later | 12 days later |
|---|---|---|---|---|---|---|---|---|
| Example 1 | 4 | 4 | 4 | 4 | 3.5 | 3.5 | 3 | 3 |
| Example 2 | 4 | 4 | 4 | 3.5 | 3.5 | 3 | 3 | 3 |
| Example 3 | 4 | 4 | 4 | 3.5 | 3 | 3 | 2.5 | 2.5 |
| Comparative Example 1 | 3 | 2 | 1.5 | 1 | 0.5 | 0.5 | 0 | 0 |
| Comparative Example 5 | 4 | 4 | 3.5 | 3 | 3 | 2.5 | 2 | 2 |

It is evident from Tables 2 and 3 that the agents for preserving freshness of cut flowers of the present invention have excellent effects to prevent wilting of petals and leaves of cut flowers of chrysanthemums.

As described in the foregoing, the agent for preserving freshness of cut flowers of the present invention is capable of prolonging the period for enjoying cut flowers substantially by the effect of preventing deterioration of freshness due to e.g. wilting of petals or leaves, or yellowing of leaves of cut flowers, of preventing the bent neck and to delay the blooming.

Further, the freshness-preserving agent for cut flowers of the present invention is transparent and odorless when diluted to a concentration for application, and it is harmless to most plants and animals.

What is claimed is:

1. An agent for preserving freshness of cut flowers, which contains, as an active ingredient, at least one water-soluble polymer selected from the group consisting of:

i) a polycondensation product obtained by a reaction of (a) at least one compound selected from the group consisting of an epihalohydrin, an alkylene dihalide, a diepoxide and a dihalogenoalkyl ether, with (b) at least one compound selected from the group consisting of an amine, a diamine and a polyamine, ii) an alkyleneimine polymer, and iii) a mixture of the polymers i) and ii) in combination with a flower freshness preserving additive.

2. The agent of claim 1, wherein the freshness preserving additive is a fungicide, a surfactant, a plant hormone or a nutrient.

3. The agent of claim 2, wherein the nutrient is an inorganic salt, a saccharide or a nitrogen source.

4. The agent of claim 3, wherein the inorganic salt is aluminum sulfate or potassium aluminum sulfate.

5. The agent of claim 3, wherein the saccharide is glucose, fructose, sorbitol or a polysaccharide.

6. The agent of claim 2, wherein the plant hormone is sitokanine, dibereline, abscisic acid or folic acid.

7. A method for preserving freshness of cut flowers, which comprises dipping the cut flowers in an aqueous solution which contains, as an active ingredient, at least one water-soluble polymer selected from the group consisting of:

i) a polycondensation product obtained by a reaction of (a) at least one compound selected from the group consisting of an epihalohydrin, an alkylene dihalide, a diepoxide and a dihalogenoalkyl ether, with (b) at least one compound selected from the group consisting of an amine, a diamine and a polyamine, ii) an alkyleneimine polymer, and iii) a mixture of the polymers i) and ii).

8. The method for preserving freshness of cut flowers according to claim 7, wherein the compound (b) is at least one amine of the following formula (1):

wherein each of $R^1$, $R^2$, $R^3$ and $R^4$ is a hydrogen atom or a $C_{1-3}$ linear or branched alkyl group, A is a $C_{1-6}$ linear or branched alkylene group, and n is an integer of from 0 to 5.

9. The method for preserving freshness of cut flowers according to claim 7, wherein the intrinsic viscosity (25° C.) of the water-soluble polymer is from 0.02 to 2 dl/g.

10. The method for preserving freshness of cut flowers according to claim 7, wherein the compound (a) is at least one member selected from the group consisting of epichlorohydrin, bromochloropropane, dibromopropane, dibromohexane, dichlorononane, dichloroethane, dichlorobutane, dichlorocyclohexane, dibromoethane, 1,3-dichloropropane, 2,2'-dichloroethyl ether, 1,3-butadiene diepoxide, 1,4-pentadiene diepoxide, 1,5-hexadiene diepoxide, 1,6-heptadiene diepoxide, 1,7-octadiene diepoxide, ethylene glycol glycidyl ether and triethylene glycidyl ether.

11. The method for preserving freshness of cut flowers according to claim 8, wherein the amine of the formula (1) is at least one member selected from the group consisting of ammonia, methylamine, dimethylamine, dipropylamine, methylethylamine, methylpropylamine, ethylpropylamine, ethylenediamine, dimethylethylenediamine, diethylethylenediamine, propylenediamine, dimethylpropylenediamine, tetramethylethylenediamine, diethylenetriamine, triethylenetriamine and tetraethylenepentamine.

12. The method for preserving freshness of cut flowers according to claim 7, wherein the water-soluble polymer is a water-soluble polymer obtained by polycondensation of at least one member selected from the group consisting of epichlorohydrin, 1,3-dichloropropane and 2,2'-dichloroethyl ether, with at least one amine selected from the group consisting of dimethylamine, tetramethylethylenediamine, diethylenetriamine and ethylene glycol diglycidyl ether.

13. The method for preserving freshness of cut flowers according to claim 7, wherein the aqueous solution which contains, as an active ingredient, the water-soluble polymer is used as a pretreating agent which is used for water uptake by cut flowers after the harvest.

14. The method for preserving freshness of cut flowers according to claim 13, wherein the pretreating agent is an aqueous solution containing from 10 to 500,000 ppm of the water-soluble polymer.

15. The method for preserving freshness of cut flowers according to claim 7, wherein the aqueous solution which contains, as an active ingredient, the water-soluble polymer, is used as a post-treating agent which is used as added to water for cut flowers.

16. The method for preserving freshness of cut flowers according to claim 15, wherein the aqueous solution used as the post-treating agent contains from .5 to 5,000 ppm of the water-soluble polymer.

* * * * *